(12) United States Patent
Class et al.

(10) Patent No.: US 8,962,562 B2
(45) Date of Patent: Feb. 24, 2015

(54) USE OF HISTONES FOR THERAPEUTIC PURPOSES

(71) Applicant: Symbiotec Genellschaft zur Erforshung auf dem Geibeit der Biotechnologie, mbH, Saarbruecken (DE)

(72) Inventors: Reiner Class, London (GB); Michael Zeppezauer, Saarbruecken (DE)

(73) Assignee: Lipoxen Technologies Incorporated, London (GB)

( * ) Notice: Subject to any disclaimer, the term of this patent is extended or adjusted under 35 U.S.C. 154(b) by 0 days.

(21) Appl. No.: 13/758,950

(22) Filed: Feb. 4, 2013

(65) Prior Publication Data

US 2014/0148391 A1     May 29, 2014

Related U.S. Application Data

(63) Continuation of application No. 11/920,050, filed as application No. PCT/EP2006/004167 on May 4, 2006, now abandoned.

(30) Foreign Application Priority Data

May 10, 2005 (DE) .......................... 10 2005 022 319

(51) Int. Cl.
    *A61K 38/00*       (2006.01)
    *A61K 38/16*       (2006.01)
    *A61K 38/17*       (2006.01)

(52) U.S. Cl.
    CPC .................. *A61K 38/1709* (2013.01)

USPC ........................................... 514/13.5; 514/1.1

(58) Field of Classification Search
None
See application file for complete search history.

(56) References Cited

U.S. PATENT DOCUMENTS

| | | | |
|---|---|---|---|
| 4,818,763 A | 4/1989 | Rusch et al. | |
| 5,182,257 A * | 1/1993 | Zeppezauer et al. | 514/19.3 |
| 5,571,686 A * | 11/1996 | Rosenberg et al. | 435/29 |
| 5,578,571 A | 11/1996 | Zeppezauer et al. | |
| 6,468,537 B1 | 10/2002 | Datta et al. | |
| 6,884,423 B1 | 4/2005 | Class et al. | |
| 7,902,146 B2 * | 3/2011 | Zeppezauer et al. | 514/19.6 |
| 2003/0017987 A1* | 1/2003 | Zeppezauer et al. | 514/12 |
| 2006/0078539 A1 | 4/2006 | Kosaka et al. | |

FOREIGN PATENT DOCUMENTS

| | | |
|---|---|---|
| DE | 19715149 A1 | 10/1998 |
| JP | H3502582 A | 6/1991 |
| JP | 2002-355048 A | 12/2002 |
| WO | 85-03003 A1 | 7/1985 |

(Continued)

OTHER PUBLICATIONS

MK Business News, Nov. 30, 2001, "Acute myeloid leukemia, a type of blood cancer," p. 1.*

(Continued)

*Primary Examiner* — Elizabeth C Kemmerer
(74) *Attorney, Agent, or Firm* — One3 IP Management, P.C.; Mary M. H. Eliason; Dean Stathakis

(57) ABSTRACT

The invention relates to the use of at least one human recombinant histone, especially at least one histone H1 subtype, and/or a therapeutic histone fraction as a basis for the treatment of thrombocytopenia.

11 Claims, 1 Drawing Sheet

(56) References Cited

FOREIGN PATENT DOCUMENTS

| WO | 8911864 | A1 | 12/1989 |
| WO | 9846252 | A1 | 10/1998 |
| WO | 02064159 | A1 | 8/2002 |
| WO | 02067907 | A1 | 9/2002 |

OTHER PUBLICATIONS

Cines, et al., Pathobiology of Secondary Immune Thrombocytopenia, NIH Pubic Access Author Manuscript, Semin Hematol. Jan. 2009; 46(1 Suppl 2): S2-14. doi:10.1053/j.seminhematol.2008,12.005.

National Cancer Institute, Chronic Lymphocytic Leukemia Treatment (PDQ®), Health Professional Version, Last Modified Apr. 16, 2014. http://www.cancer.gov/cancertopics/pdq/treatment/CLL/healthprofessional.

Tfayli, et al., Management of Thrombocytopenia in Patients with Leukemia, CME/CE Released Jan. 28, 2008. www.medscape.org/viewarticle/569207.

Berger, S "Platelet Function: A review Part II, Abnormal Function" C.M.A Journal, Jun. 20, 1970, vol. 102, pp. 1379-1383.

Bug, G. et al., "Valproic acid stimulates proliferation and self-renewal of hematopoietic stem cells," Cancer Res, 2005, vol. 65, No. 7, p. 2537-41.

Class et al., Histone H1 Suppresses Tumor Growth of Leukemia Cells In Vitro, Ex Vivo and in an Animal Model Suggesting Extracellular Functions of Histones, Am J Clin Oncol (CCT) 19(5): 522-531, 1996.

Ellison, Norig, "Diagnosis and Management of Bleeding Disorders." Anesthesiology 47:171-180 (1977).

Goodman, R. et al., "Hematopoietic stem cells: effect of preirradiation, bleeding, and erythropoietin on thrombopoietic differentiation," Blood 1997, vol. 49, Nol. 2, p. 253-61.

Gordon & Hoffman, "Growth Factors Affecting Human Thrombocytopoiesis: Potential Agents for the Treatment of Thrombocytopenia." Blood, V.80, No. 2 (Jul. 15, 1992): pp. 302-307.

International Preliminary Report on Patentability PCT/EP2006/004167, Issue Date Jan. 24, 2008.

Kuter, David, "The Physiology of Platelet Production." Stem Cells, 1996; 14(suppl 1):88-101.

Reimann, Hobart, "Haemocytic periodicity and periodic disorders: Periodic Neutropenia, thrombocytopenia, lymphocytosis and anaemia." Postgraduate Medical Journal (Jul. 1971) 47, 504-510.

Ruirong et al., "Treatment of Acute Myeloid Leukemia by Concomitant Use of (in chinese)" Clinical Journal of Traditional Chinese Medicine, 2005, vol. 26, No. 1, 32-5.

Semina, V. "Effect of Histone on Hematopoietic stem cells (cfu-s) in normal and irradiated organism." Radiats Biol Radioecol. 1994, 34(4-5) 544-9.

Valiron, O. et al. Histone H1(0) expression is restricted to progenitor cells during human hematopoiesis, Eur. J. Cell. Biol., 1997, vol. 72, No. 1 p. 39-45.

\* cited by examiner

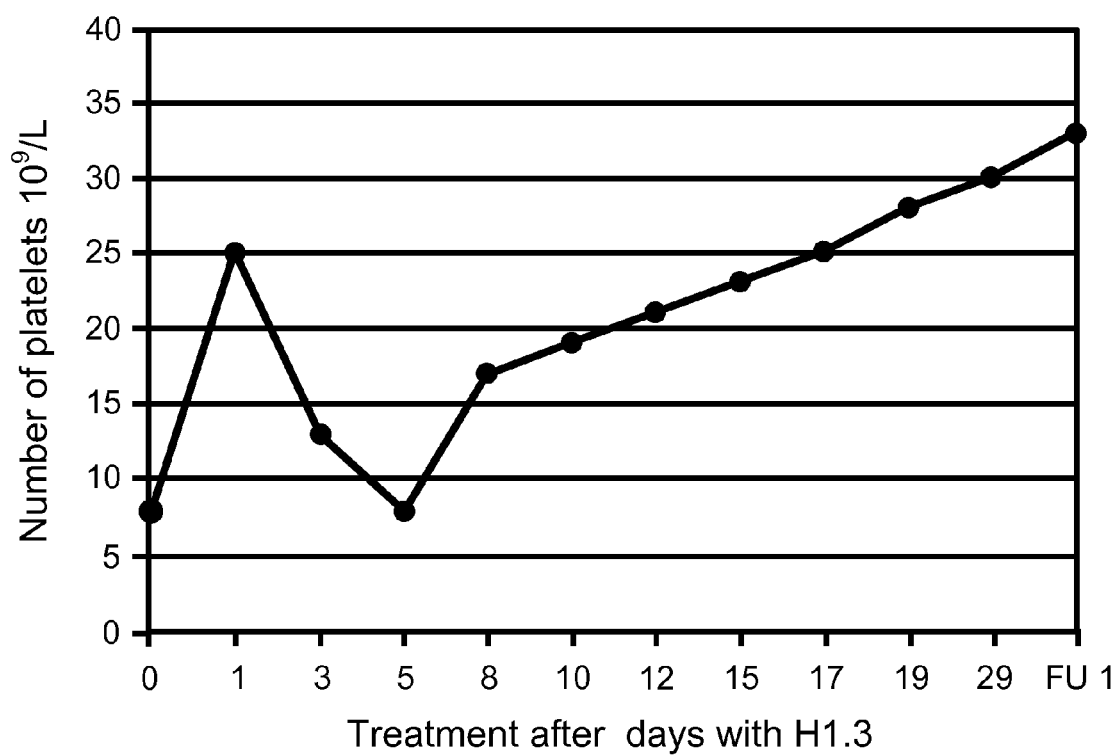

USE OF HISTONES FOR THERAPEUTIC PURPOSES

The present application is a continuation of U.S. patent application Ser. No. 11/920,050; filed Nov. 6, 2008, now abandoned, which is a national stage entry of PCT/EP2006/004167; filed May 4, 2006, which claims priority to DE 10 2005 022 319.2; filed May 10, 2005, all which are hereby incorporated by reference.

The invention relates to the use of at least one human recombinant histone of H1 subtype and/or of its therapeutically effective segment, especially histone H1.3 for therapeutic purposes.

The use of therapeutic active substances based on human recombinant histone H1 subtypes for the treatment of cancers, e.g. leukemia, is disclosed in the article by Reiner Class et al. in Am. J. Clin. Oncol. (CCT) vol. 19 No. 5 1996 and European patent application 98919254.7.

The effect of histone H1 and H2A/H2B fractions from calf thymus on hematopoietical stem cells (CFU-S) in normal and radioactively irradiated rats was described in a Russian article by Semina O. V. et al. in Radiatsionnaia Biologiia, Radioecologiia 34 (4-5), 1994, July-October In complex pathological conditions such as acute myeloid leukemia, there is frequently observed to be a thrombocytopenia which may even be enhanced by a chemotherapeutic treatment of the leukemia. Thrombocytopenia is, however, also observed with other etiology. Since thrombocytopenia may lead to life-threatening internal hemorrhages, therapies for various pathological symptoms which may be the cause of the thrombocytopenia are frequently made particularly difficult.

BRIEF SUMMARY

It was therefore an object of the invention to find an active substance which can be used therapeutically for thrombocytopenia in order thus also to improve substantially the success of curing the basic symptom as inducer of the thrombocytopenia.

BRIEF DESCRIPTION OF THE DRAWINGS

FIG. 1 (hereinafter "FIG. 1") shows the effect of the active substances of the invention in a 0.9% NaCl solution at, 37.5 mg/qm² of body surface area on the thrombocytopenia of a patient.

DETAILED DESCRIPTION

It has been possible according to the invention to achieve the object by using for the therapy of thrombocytopenia inter alia as a result of faulty stem cell differentiation or weakened proliferation of megakaryocytes an active substance based on at least one human recombinant histone (especially at least one histone of H1 subtype) and/or its therapeutically effective segment.

This applies especially to a thrombocytopenia as concomitant manifestation of a hematological disorder.

It is moreover possible to employ the therapeutic method of the invention for the treatment of thrombocytopenia during or after chemotherapy for the treatment of a hematological disorder, especially acute myeloid leukemia.

It has surprisingly been possible to show that the active substance of the invention shows on the one hand a positive result in the treatment of a hematological disorder such as leukemia, but on the other hand also a positive result in the treatment of the thrombocytopenia associated with the hematological disorders.

It was thus possible with one and the same active substance to note both a regression in the leukemia and an increase in platelets.

It was possible to achieve therapeutic trial results also on patients with human recombinant histone H1.3, it having been possible to reduce markedly the number of pathological tumor cells in an AML patient and, at the same time, to increase substantially platelet production, whereby it was possible to improve substantially the prospects of curing the patient.

The trial results are reproduced in more detail below, the active substance used in this case, based on human recombinant H1.3 concentrations 37.5 mg/qm² of body surface area etc., having been administered in a 0.9% NaCl solution intravenously 3 times a week over a period of about 4 hours.

FIG. 1 shows the effect of the active substances of the invention in a 0.9% NaCl solution at, 37.5 mg/qm² of body surface area on the thrombocytopenia of a patient.

The platelets in peripheral blood are on the ordinate in a number of from 0 to $40 \times 10^9$. Treatment with active substance of the invention for three weeks is shown on the abscissa, the platelet count measured for the patient before the first treatment being greatly reduced at about $8 \times 10^9$. Then in each case three drip infusions take place per week with in each case 4 hours per infusion, with the 1st to 3rd infusion on the 1st, 3rd and 5th day in the first week, with the 4th to 6th infusion on the 8th, 10th and 12th day in the second week and finally with the 7th to 9th infusion on the 15th, 17th and 19th day in the 3rd week. On the 29th day after the first infusion, a control measurement of the platelet count took place without a further infusion with the active substance of the invention. At a later time FU1, the patient was discharged with an almost normal platelet count of about $34 \times 10^9$, without an active substance of the invention having been supplied even once. This value lay outside the need to supply stored blood. The patient was asked to attend a follow-up examination with the possibility of resumption of treatment if the platelet count has not improved further on its own or had even deteriorated. The results of the follow-up examination are not shown here.

The appended FIG. 1 shows at the start of the second week up to conclusion of the treatment in the third week a jump in the platelet count after the 5th day of treatment and then a continuous rise in the platelet count from the 8th to the subsequent 19th day of treatment and a further slower rise in the platelet count at the first control examination on the 29th day and at a later discharge day FU1 of the patient without further addition of the active substance of the invention, the finally measured platelet count being, as already stated, about $32.5 \times 10^9$.

The invention is not restricted to the use of human recombinant H1.3. Because of the close relationship of the H1 subtypes, it is obvious to a skilled worker also to employ as active substance other human recombinant H1 subtypes as basis for the active substance of the invention.

Following the successful therapy of patients with a thrombocytopenia, here as concomitant syndrome of an AML leukemia, with human recombinant histone H1.3, it is particularly obvious to a skilled worker also to employ other recombinant H1 subtypes as alternative active substances singly or in combination according to the invention.

The active substance of the invention preferably consists of the complete unshortened subtypes of histone proteins. However, it is also obvious to a skilled worker to look for the therapeutically effective segment, of which he is capable directly on the basis of his expert knowledge and experience without outstanding innovative contributions being necessary in this case. Such therapeutically effective histone segments therefore lie within the range of equivalents of the teaching of the invention disclosed herein.

The invention further discloses the therapeutic teaching of employing, when there is a threatening or incipient primary disorder which, experience has shown, may result in thrombocytopenia, the active substance of the invention prophylactically against a threatening thrombocytopenia even if, unlike leukemia, the active substance of the invention is not effective against the primary disorder.

The invention claimed is:

1. A method for treating of a thrombocytopenia in a patient in need thereof, the method comprising the step of administering to the patient a pharmaceutical composition comprising at least one recombinant histone H1 or a therapeutically active histone H1 segment, wherein administration of the pharmaceutical composition increases the number of platelets in the peripheral blood, thereby treating the thrombocytopenia.

2. The method according to claim 1, wherein the thrombocytopenia results from a hematological disorder.

3. The method according to claim 2, wherein the hematological disorder is a leukemia.

4. The method according to claim 3, wherein the leukemia is an acute myeloid leukemia.

5. The method according to claim 1, wherein the treatment of the thrombocytopenia occurs concurrently with or after a therapy for a hematological disorder.

6. The method according to claim 5, wherein the therapy is a chemotherapy.

7. The method according to claim 5, wherein the hematological disorder is a leukemia.

8. The method according to claim 5, wherein the leukemia is an acute myeloid leukemia.

9. The method according to claim 1, wherein the histone is a histone H1.3.

10. A method for treating thrombocytopenia in a patient in need thereof, the method comprising: administering to the patient at least three doses of a pharmaceutical composition comprising at least one recombinant histone H1 or a therapeutically active histone H1 segment during a period of at least 8 days, wherein administration of the pharmaceutical composition increases the number of platelets in the peripheral blood, thereby treating the thrombocytopenia.

11. A method for treating thrombocytopenia in a patient in need thereof caused by a primary disorder, comprising: administering to the patient a pharmaceutical composition comprising at least one recombinant histone H1 or a therapeutically active histone H1 segment, wherein the histone H1 is not effective to treat the primary disorder.

* * * * *